United States Patent
Lamielle et al.

(10) Patent No.: US 6,200,344 B1
(45) Date of Patent: Mar. 13, 2001

(54) INRAOCULAR LENSES

(75) Inventors: Helene Lamielle, Irvine; Laurent Hoffmann, Foothill Ranch, both of CA (US); Vincent Blanchard, Crapponne (FR)

(73) Assignee: Bausch & Lomb Surgical, Inc., Claremont, CA (US)

(*) Notice: Subject to any disclaimer, the term of this patent is extended or adjusted under 35 U.S.C. 154(b) by 0 days.

(21) Appl. No.: 09/301,883

(22) Filed: Apr. 29, 1999

(51) Int. Cl.$^7$ ........................................... A61F 2/16
(52) U.S. Cl. .................. 623/6.51; 623/6.11; 623/6.38; 623/6.4; 623/6.43
(58) Field of Search .................. 623/6.11, 6.38, 623/6.4, 6.43, 6.45, 6.51

(56) References Cited

U.S. PATENT DOCUMENTS

| | | | |
|---|---|---|---|
| Re. 31,640 | 8/1984 | Freeman | 623/6 |
| Re. 32,525 | 10/1987 | Pannu | 623/6 |
| Re. 33,039 | 8/1989 | Arnott | 623/6 |
| 3,721,657 | 3/1973 | Seiderman et al. | 623/6 |
| 3,792,028 | 2/1974 | Seiderman | 623/6 |
| 3,961,379 | 6/1976 | Highgate | 623/6 |
| 4,073,015 | 2/1978 | Peyman et al. | 623/6 |
| 4,242,762 | 1/1981 | Tennant | 623/6 |
| 4,249,272 | 2/1981 | Poler | 623/6 |
| 4,254,509 | 3/1981 | Tennant | 623/6 |
| 4,254,510 | 3/1981 | Tennant | 623/6 |
| 4,261,065 | 4/1981 | Tennant | 623/6 |
| 4,277,852 | 7/1981 | Poler | 623/6 |
| 4,315,336 | 2/1982 | Poler | 623/6 |
| 4,316,293 | 2/1982 | Bayers | 623/6 |
| 4,377,873 | 3/1983 | Reichart, Jr. | 623/6 |
| 4,403,353 | 9/1983 | Tennant | 623/6 |
| 4,424,597 | 1/1984 | Schlegel | 623/6 |
| 4,446,581 | 5/1984 | Blake | 623/6 |
| 4,556,998 | 12/1985 | Siepser | 623/6 |
| 4,573,998 | 3/1986 | Mazzocco | 623/6 |
| 4,575,374 | 3/1986 | Anis | 623/6 |
| 4,575,878 | 3/1986 | Dubroff | 623/6 |
| 4,585,456 | 4/1986 | Blackmore | 623/6 |
| 4,605,409 | 8/1986 | Kelman | 623/6 |
| 4,605,411 | 8/1986 | Fedorov et al. | 623/6 |

(List continued on next page.)

FOREIGN PATENT DOCUMENTS

| | | |
|---|---|---|
| 331730/84 | 8/1983 | (AU). |
| 2717706 | 4/1977 | (DE). |
| 3439551A1 | 10/1984 | (DE). |
| 0136807 | 8/1984 | (EP). |
| 391452B1 | 8/1984 | (EP). |
| 0118985 | 9/1984 | (EP). |
| 1103399 | 11/1955 | (FR). |
| 2 748 200 | 11/1997 | (FR). |
| 2 765 797 | 1/1999 | (FR). |
| 2114315A | 8/1983 | (GB). |
| 2151371A | 7/1985 | (GB). |
| WO 87/01931 | 4/1987 | (WO). |

Primary Examiner—Dinh X. Nguyen
(74) Attorney, Agent, or Firm—Rita D. Vacca

(57) ABSTRACT

A refractive intraocular lens including an optic portion having an outer peripheral edge and two or more but preferably two balanced opposed looped haptic elements. Each looped haptic element is formed to have two broad connecting portions, two radial orientation portions, two spring portions and a linking portion for supporting the optic portion in a patient's eye. The two broad connecting portions of each looped haptic element is permanently connected to the outer peripheral edge of the optic portion. Each looped haptic element is likewise formed to have greater resistance to bending in a plane generally parallel to an eye's optical axis than in a plane generally perpendicular to the eye's optical axis. The intraocular lens is so designed to exhibit less than approximately 1.0 mm axial displacement or tilting of the optic portion along the eye's optical axis under a compression force suitable to effect a 1.0 mm in diameter compression in overall length of the intraocular lens.

18 Claims, 4 Drawing Sheets

U.S. PATENT DOCUMENTS

| | | |
|---|---|---|
| 4,615,702 | 10/1986 | Koziol et al. .............................. 623/6 |
| 4,629,460 | 12/1986 | Dyer ......................................... 623/6 |
| 4,629,462 | 12/1986 | Feaster ...................................... 623/6 |
| 4,634,441 | 1/1987 | Clayman et al. ......................... 623/6 |
| 4,642,113 | 2/1987 | Dubroff ..................................... 623/6 |
| 4,642,116 | 2/1987 | Clayman et al. ......................... 623/6 |
| 4,664,666 | 5/1987 | Barrett ...................................... 623/6 |
| 4,673,406 | 6/1987 | Schlegel .................................... 623/6 |
| 4,676,791 | 6/1987 | LeMaster et al. ........................ 623/6 |
| 4,676,792 | 6/1987 | Praeger ..................................... 623/6 |
| 4,687,485 | 8/1987 | Lim et al. ................................. 623/6 |
| 4,718,904 | 1/1988 | Thornton ................................... 623/6 |
| 4,718,906 | 1/1988 | Mackool .................................... 623/6 |
| 4,725,277 | 2/1988 | Bissonette ................................. 623/6 |
| 4,734,095 | 3/1988 | Siepser ...................................... 623/6 |
| 4,769,035 | 9/1988 | Kelman ..................................... 623/6 |
| 4,781,717 | 11/1988 | Grendahl ................................... 623/6 |
| 4,787,904 | 11/1988 | Severin et al. ............................ 623/6 |
| 4,816,030 | 3/1989 | Robinson ................................... 623/6 |
| 4,863,466 | 9/1989 | Schlegel .................................... 623/6 |
| 4,932,970 | 6/1990 | Portney ..................................... 623/6 |
| 4,936,850 | 6/1990 | Barrett ...................................... 623/6 |
| 4,997,442 | 3/1991 | Barrett ...................................... 623/6 |
| 5,002,568 | 3/1991 | Katzen ...................................... 623/6 |
| 5,047,052 | 9/1991 | Dubroff ..................................... 623/6 |
| 5,066,301 | 11/1991 | Wiley ........................................ 623/6 |
| 5,071,432 | 12/1991 | Baikoff ..................................... 623/6 |
| 5,078,742 | 1/1992 | Dahan ....................................... 623/6 |
| 5,092,880 | 3/1992 | Ohmi ........................................ 623/6 |
| 5,100,226 | 3/1992 | Freeman ................................... 623/6 |
| 5,108,429 | 4/1992 | Wiley ........................................ 623/6 |
| 5,133,749 | 7/1992 | Nordan ...................................... 623/6 |
| 5,147,395 | 9/1992 | Willis ........................................ 623/6 |
| 5,171,266 | 12/1992 | Wiley et al. ............................... 623/6 |
| 5,196,026 | 3/1993 | Barrett et al. ............................. 623/6 |
| 5,197,981 | 3/1993 | Southard ................................... 623/6 |
| 5,203,788 | 4/1993 | Wiley ........................................ 623/6 |
| 5,203,790 | 4/1993 | McDonald ................................ 623/6 |
| 5,211,662 | 5/1993 | Barrett et al. ............................. 623/6 |
| 5,217,491 | 6/1993 | Vanderbilt ................................. 623/6 |
| 5,222,981 | 6/1993 | Werblin .................................... 623/6 |
| 5,258,025 | 11/1993 | Fedorov et al. .......................... 623/6 |
| 5,336,261 | 8/1994 | Barrett et al. ............................. 623/6 |
| 5,476,514 | 12/1995 | Cumming ................................. 623/6 |
| 5,716,403 | 2/1998 | Tran et al. ................................. 623/6 |

INRAOCULAR LENSES

FIELD OF THE INVENTION

The present invention relates to intraocular lenses (IOLs) and a method for making and using the same. More particularly, the present invention relates to IOLs designed primarily for refractive correction in aphakic eyes. IOLs made in accordance with the present invention are used in aphakic eyes to replace a surgically removed diseased natural lens, such as in the case of cataracts. IOLs made in accordance with the present invention may also be used in phakic eyes in conjunction with a natural lens to correct vision impairments.

BACKGROUND OF THE INVENTION

IOL implants have been used for years in aphakic eyes as replacements for diseased natural crystalline lenses that have been surgically removed from the eyes. Many different IOL designs have been developed over past years and proven successful for use in aphakic eyes. The successful IOL designs to date primarily include an optic portion with supports therefor, called haptics, connected to and surrounding at least part of the optic portion. The haptic portions of an IOL are designed to support the optic portion of the IOL in the lens capsule or posterior chamber of an eye when used in aphakic eyes or in the posterior or anterior chamber of an eye when used in phakic eyes.

Commercially successful IOLs have been made from a variety of biocompatible materials, ranging from more rigid materials such as polymethylmethacrylate (PMMA) to softer, more flexible materials capable of being folded or compressed such as silicones, certain acrylics, and hydrogels. Haptic portions of the IOLs have been formed separately from the optic portion and later connected thereto through processes such as heat, physical staking and/or chemical bonding. Haptics have also been formed as an integral part of the optic portion in what is commonly referred to as "single-piece" IOLs.

Softer, more flexible IOLs have gained in popularity in more recent years due to their ability to be compressed, folded, rolled or otherwise deformed. Such softer IOLs may be deformed prior to insertion thereof through an incision in the cornea of an eye. Following insertion of the IOL in an eye, the IOL returns to its original pre-deformed shape due to the memory characteristics of the soft material. Softer, more flexible IOLs as just described may be implanted into an eye through an incision that is much smaller, i.e., 2.8 to 3.2 mm, than that necessary for more rigid IOLs, i.e., 4.8 to 6.0 mm. A larger incision is necessary for more rigid IOLs because the lens must be inserted through an incision in the cornea slightly larger than the diameter of the inflexible IOL optic portion. Accordingly, more rigid IOLs have become less popular in the market since larger incisions have been found to be associated with an increased incidence of postoperative complications, such as induced astigmatism.

After IOL implantation in either phakic or aphakic applications, both softer and more rigid IOLs are subject to compressive forces exerted on the outer edges thereof, which typically occur when an individual squints or rubs the eye. These compressive forces may result in decentration of the IOL and distortion of the visual image. Compressive forces exerted on an IOL also tend to cause the lens to tilt or have axial displacement of the IOL along the optical axis of an eye. Movement of an IOL along the optical axis of an eye has the potential to cause the IOL to contact and damage delicate eye tissues. Also, IOLs of current designs, whether formed of either softer or more rigid materials, tend to deflect along the optical axis of an eye when the haptics are compressed. IOL manufacturers provide a wide range of IOL sizes to more precisely fit IOLs to each particular patient's eye size. Providing a wide range of IOL sizes is an attempt to minimize the potential for axial displacement of the IOL along the optical axis of an eye.

Because of the noted shortcomings of current IOL designs, there is a need for IOLs designed to minimize tilt or axial displacement of the IOL optic portion along the optical axis of the eye when compressive forces are exerted against the outer edges thereof. By lessening an IOL's movement along the optical axis of an eye, more certain refractive correction may be achieved and the risk of tissue damage may be reduced.

SUMMARY OF THE INVENTION

An intraocular lens (IOL) made in accordance with the present invention has an optic portion with an outer peripheral edge and two, three or four, but preferably two, looped haptic elements for supporting the optic portion in a patient's eye. The subject IOL is balanced having preferably one looped haptic element formed on one edge of the optic and the other looped haptic element formed on an opposed edge of the optic. However, alternative balanced embodiments having three or four looped haptic elements are also considered to be within the scope of the present invention. In accordance with the present invention, each of the looped haptic elements has two broad connecting portions, two radial orientation portions, two spring portions and a linking portion connecting the two spring portions. The two broad connecting portions of each looped haptic element are connected to the outer peripheral edge of the optic portion. Each looped haptic element forms a large fenestration to enhance capsular fixation once within an eye. The looped haptic elements' spring portions and linking portions are designed to engage an inner surface of a patient's eye.

Each looped haptic element's broad connecting portions are designed to achieve optimal optic stability by avoiding tilt and axial displacement. Within these broad connecting portions, each looped haptic element is designed to bend in a plane generally perpendicular to the optical axis of an eye rather than in a plane generally parallel to the optical axis of an eye. By providing looped haptic elements with this type of flexibility characteristic, the present IOL tends to have maximized stability within an eye. The flexibility characteristic of the subject looped haptic elements relative to the optic portion eliminates unacceptable tilting or axial displacement of the optic portion along the optical axis when compressive forces are exerted against the looped haptic elements of the IOL.

Accordingly, it is an object of the present invention to provide intraocular lenses for use in aphakic or phakic eyes.

Another object of the present invention is to provide intraocular lenses for use in aphakic or phakic eyes with flexibility characteristics which maximize stability thereof.

Another object of the present invention is to provide intraocular lenses for use in aphakic or phakic eyes, which minimize tilt or axial displacement of the optic portions of the lenses along the optical axis of the eyes.

Another object of the present invention is to provide intraocular lenses for use in aphakic or phakic eyes, which minimize damage to tissues in the interior of the eyes.

Still another object of the present invention is to provide intraocular lenses, which are resistant to decentration within the eyes.

DETAILED DESCRIPTION OF THE INVENTION

Figure 1:
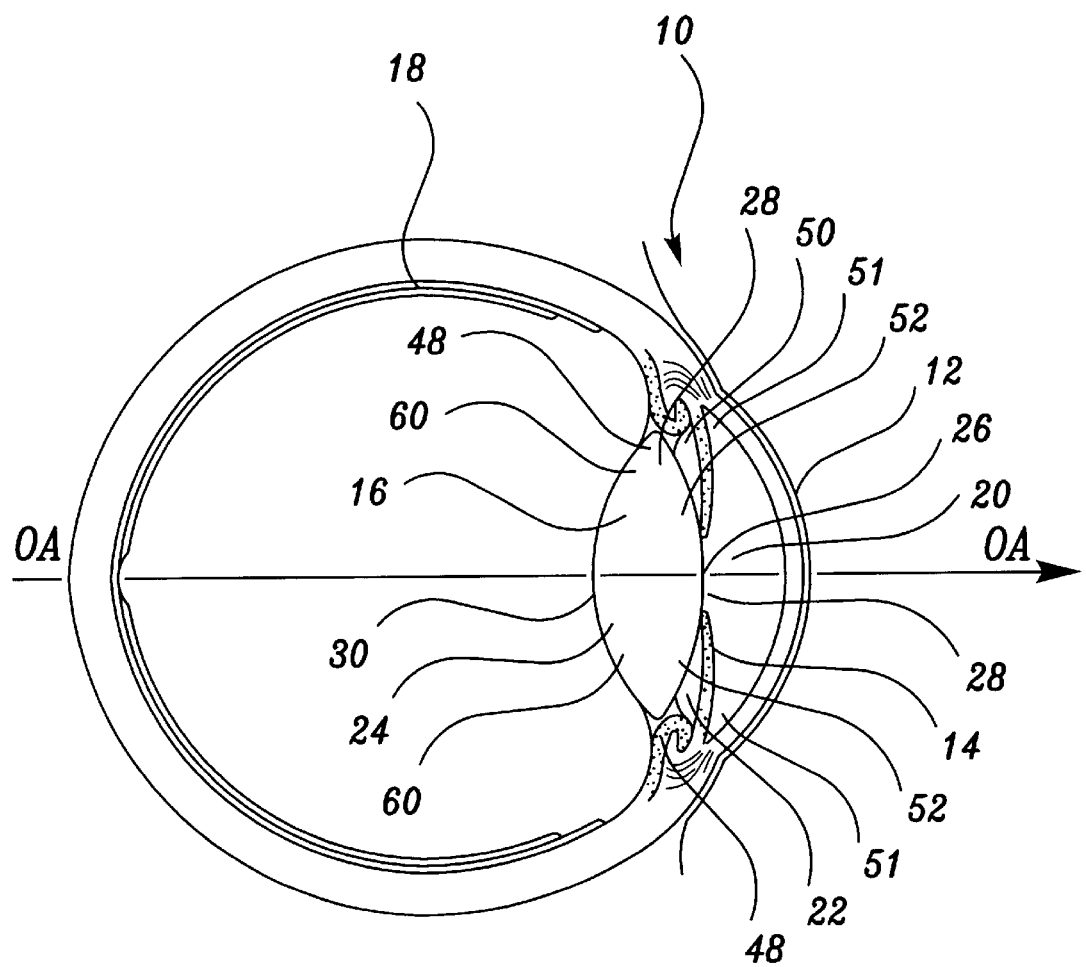
FIG. 1 is a schematic representation of the interior of a human eye including a natural lens.

FIG. 1 illustrates a simplified diagram of an eye 10 showing landmark structures relevant to the implantation of an intraocular lens of the present invention. Eye 10 includes an optically clear cornea 12 and an iris 14. A natural crystalline lens 16 and a retina 18 are located behind the iris 14 of eye 10. Eye 10 also includes anterior chamber 20 located in front of iris 14 and posterior chamber 22 located between iris 14 and natural lens 16. IOLs of the present invention are preferably implanted into lens capsule 24 or posterior chamber 22 to refract light after a diseased natural lens 16 has been surgically removed (aphakic application). Eye 10 also includes an optical axis OA—OA that is an imaginary line that passes through the optical center 26 of anterior surface 28 and posterior surface 30 of lens 16. Optical axis OA—OA in the human eye 10 is generally perpendicular to a portion of cornea 12, natural lens 16 and retina 18.

Figure 2:
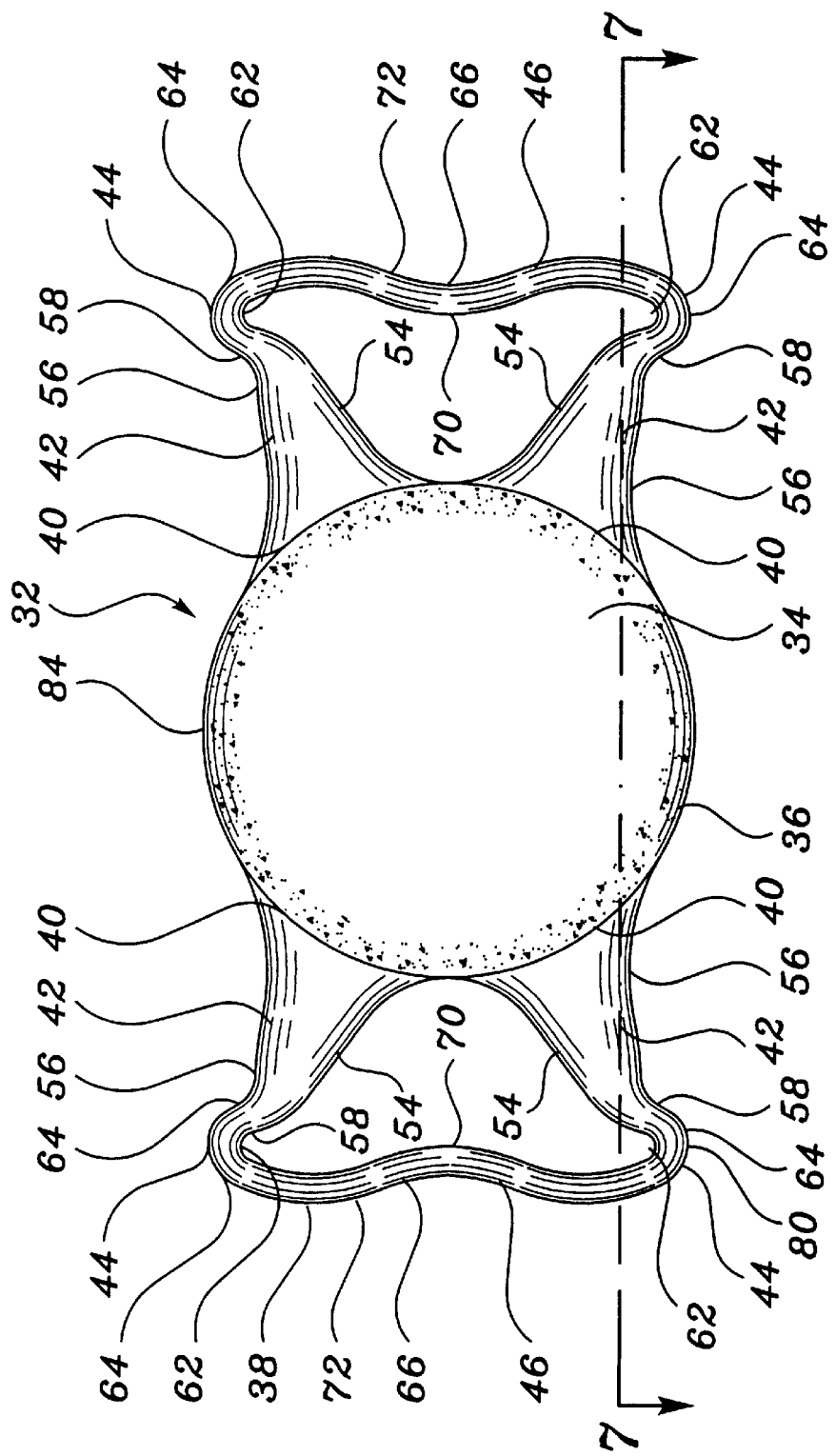
FIG. 2 is a plan view of an IOL with an optic and two looped haptic elements made in accordance with the present invention.
Figure 3:
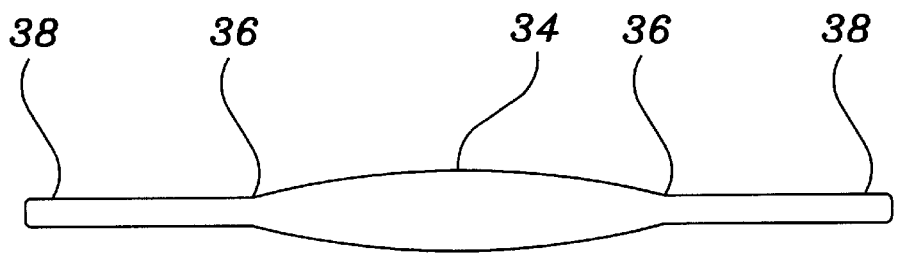
FIG. 3 is a side view of the IOL of FIG. 2.

The IOL of the present invention, as best illustrated in FIGS. 2 and 3, is identified by reference numeral 32. IOL 32 is preferably designed for implantation preferably in lens capsule 24 or posterior chamber 22 of a patient's aphakic eye 10. However, IOL 32 may likewise be implanted in anterior chamber 20 or posterior chamber 22 of a patient's phakic eye 10. IOL 32 has an optic portion 34 with an outer peripheral edge 36. Preferably integrally formed on peripheral edge 36 of optic portion 34 are two opposed looped haptic elements 38, each having two broad connecting portions 40, two radial orientation portions 42, two spring portions 44 and a linking portion 46. Broad connecting portions 40 are preferably integrally formed with and permanently connected to outer peripheral edge 36 of optic portion 34. Alternatively however, looped haptic elements 38 may be attached to optic portion 34 by staking, chemical polymerization or other methods known to those skilled in the art.

In accordance with the present invention, each looped haptic element 38 is designed to preferably engage inner surfaces 48 in lens capsule 24, surfaces 50 in posterior chamber 22 or surfaces 51 in anterior chamber 20. Looped haptic elements 38 are designed so that when IOL 32 is implanted in a patient's eye 10 and held in place through compressive forces exerted by inner surfaces 48, 50, or 51, looped haptic elements 38 flex to accommodate the particular size of eye 10. Looped haptic elements 38 are designed to be resistant to flexing and tilting in a plane generally parallel to that of optical axis OA—OA of eye 10. By designing this type of flexibility characteristic into looped haptic elements 38, IOL 32 may be manufactured in one or a few standard sizes and be a suitable fit for most sizes of patients' eyes 10. The flexibility characteristic of looped haptic elements 38 also minimize axial displacement of optic portion 34 in a direction along optical axis OA—OA of eye 10.

Broad connecting portions 40 of looped haptic elements 38 attach the looped haptic elements 38 to optic portion 34 of IOL 32. The broad connecting portions 40 are designed to be broad to increase rigidity and to minimize axial displacement or tilting of IOL 32. Broad connecting portions 40 likewise prevent the snagging or catching of eye 10 structures such as the rhexis 52 on optic 34. Each broad connecting portion 40 preferably measures to equal 10 to 20 percent of the circumference of the optic portion 34. For phakic use, IOL 32 may optionally be vaulted at broad connection portions 40 to have an angulation of 0 to 10 degrees but preferably 4 to 5 degrees.

Radial orientation portions 42 of looped haptic elements 38 have interior surfaces 54 and exterior surfaces 56. Interior surfaces 54 and exterior surfaces 56 are formed with an outward curve to increase the stability of IOL 32 when implanted in eye 10. Outer ends 58 of radial orientation portions 42 are of a significantly smaller width than that of radial orientation portions 42 at broad connecting portions 40 to minimize the surface area thereof. The surface area of outer ends 58 is designed to be as small as possible to minimize the IOL's 32 contact with the lens capsule's 24 equatorial germination zone 60 thereby decreasing cellular growth and posterior capsular opacification of IOL 32. The width of outer ends 58 is also designed to be smaller than that of the thickness of looped haptic elements 38 to allow for flexing of spring portions 44 in a plane perpendicular to optical axis OA—OA of eye 10.

Spring portions 44 have an interior surface 62 and an exterior surface 64. Spring portions 44 are designed to absorb compressive forces exerted by the eye 10 and maintain IOL alignment within lens capsule 24. Spring portions 44 when compressed upon absorption of compressive forces deform whereby interior surfaces 62 may abut outer ends 58. Also, when placed under sufficient compressive forces, each spring portion 44 may deflect outwardly in a direction away from its adjacent spring portion 44 and downwardly in a direction toward optic portion 34 to absorb such forces and avoid undesirable flexing and tilting in a plane parallel to the optical axis OA—OA of eye 10.

Linking portions 46 connect adjacent spring portions 44 to form a looped haptic element 38. Linking portions 46 are slightly bowed at preferably less than 20 degrees but more preferably at less than 10 degrees but greater than 1 degree inwardly toward optic portion 34 to form depressions 66. Upon one or more spring portions 44 being deflected outwardly in a direction away from its adjacent spring portion 44 and downwardly in a direction of optic portion 34 when placed under compressive forces, depression 66 of linking portion 46 looses its bow and becomes more linear.

Fenestration 68 defined by interior surfaces 54 and 62, and interior surfaces 70 of linking portion 46 enhances fixation of IOL 32 within lens capsule 24, posterior chamber 22 or anterior chamber 20.

Compressive forces of differing magnitudes within the range of approximately 2 to 8 mN exerted against looped haptic elements 38 effecting an approximately 2.0 mm in overall length compression of IOL 32, such as that caused by differing eye sizes or compressive forces by the eye 10, results in less than approximately 1.0 mm, but more preferably less than approximately 0.5 mm and most preferably less than approximately 0.3 mm axial displacement or tilting of optic portion 34 along optical axis OA—OA in an eye 10. Under like compressive forces, IOLs known in the art result in approximately 2.0 mm axial displacement of the optic portion along the optical axis in the eye, which may damage delicate tissues therein. The unique design of IOL 32 achieves significantly minimized axial displacement or tilting of optic portion 34 to protect the eye 10 from damage when compressive forces are applied to eye 10.

Figure 4:
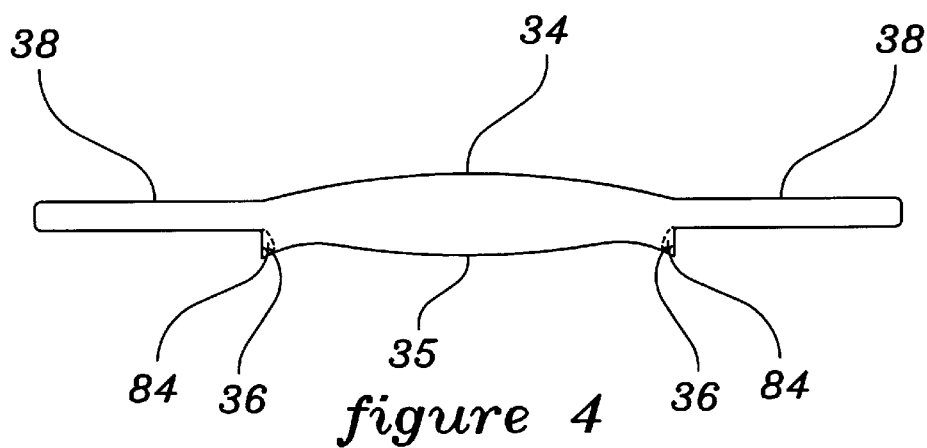
FIG. 4 is a side view of the IOL of FIG. 2 with sharper peripheral edges on a posterior surface of the optic.
Figure 5:
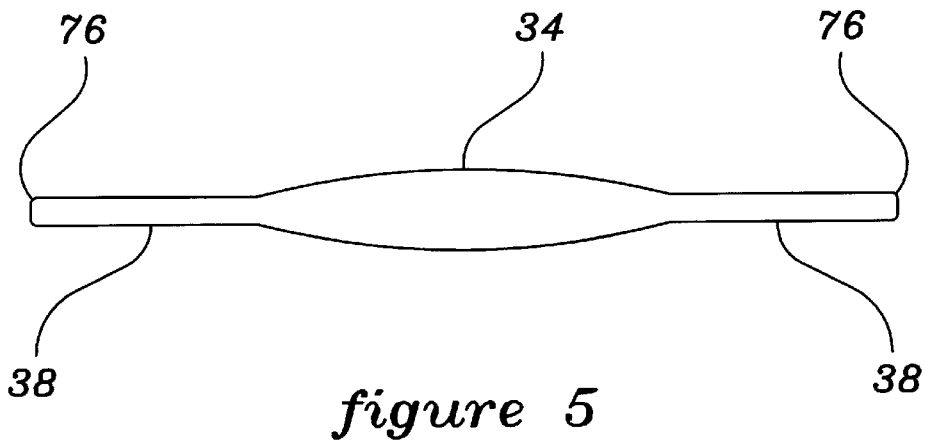
FIG. 5 is a side view of the IOL of FIG. 2 with sharper edges on the two looped haptic elements.
Figure 6:
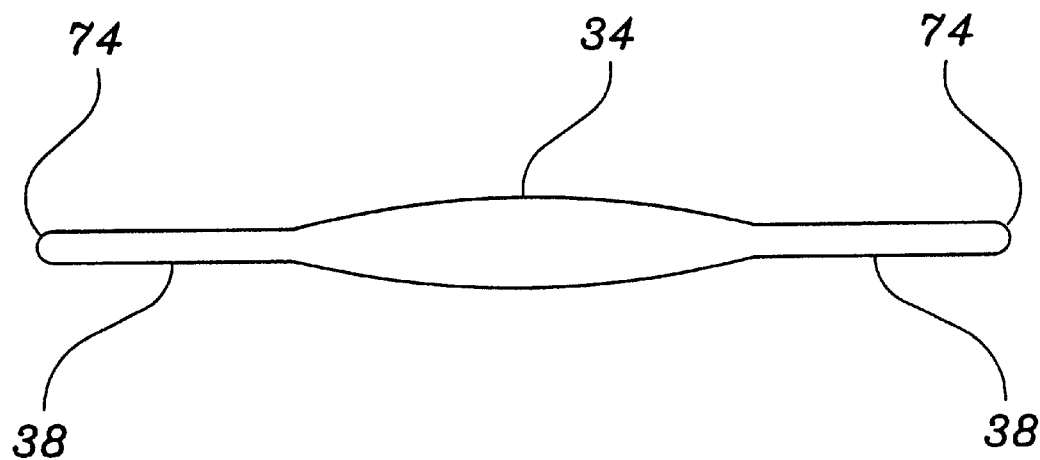
FIG. 6 is a side view of the IOL of FIG. 2 with rounder edges on the two looped haptic elements.

The flexibility characteristic of looped haptic elements 38 of IOL 32 as described above is achieved through the unique design thereof. The exterior surface 72 of linking portion 46 and the exterior surface 64 of spring portions 44 may be formed with either rounded edges 74 depicted in FIG. 6 for a smoother fit with inner surfaces 48, 50, or 51 or more defined, sharper edges 76 depicted in FIG. 5 to provide a barrier to prevent cellular migration and growth. Another feature which may be incorporated into the subject lens is a sharper peripheral edge 36 on posterior surface 35 of optic portion 34 as depicted in FIG. 4 to provide a barrier to prevent cellular migration and growth.

The subject IOL 32 is preferably produced having an optic portion 34 approximately 4.5 to 9.0 mm, but preferably approximately 5.0 to 7.0 mm and most preferably 6.0 mm in diameter and approximately 0.5 mm to 1.0 mm, but preferably approximately 0.6 to 0.8 mm and most preferably 0.7 mm in thickness at peripheral edge 36. The size of optic portion 34 may likewise vary depending on the intended use, such as a smaller size for hyperopic use. Looped haptic elements 38 increase or decrease in overall length depending upon the diameter of optic portion 34 so that the overall length of IOL 32 remains generally consistent. As the diameter of optic portion 34 increases, the overall length of looped haptic elements 38 decrease. Likewise, as the diameter of optic portion 34 decreases, the overall length of looped haptic elements 38 increase. In general, looped haptic elements 38 are formed to be approximately 8.5 to 13.5 mm, but preferably approximately 9.0 to 12.0 mm and most preferably approximately 10.5 mm in overall length. Such overall length is obtained measuring from the center of broad connecting portion 40 around through the center of looped haptic element 38 to the center of adjacent broad connecting portion 40. The width of looped haptic elements 38 measuring the distance between the outer tips 80 of spring portions 44 is approximately 4.5 to 9.0 mm, but preferably approximately 5.0 to 6.5 mm and most preferably 5.5 mm. Looped haptic elements 38 preferably have the same thickness throughout their entire length which is approximately 0.2 to 0.9 mm, but preferably approximately 0.3 to 0.7 mm and most preferably approximately 0.55 mm. Looped haptic elements 38 could also however be of varying thickness without departing from the scope of the present invention. Spring portions 44 measuring the distance from outer end 58 to exterior surface 64 at linking portion 46 are approximately 0.4 to 1.5 mm, but preferably approximately 0.6 to 1.2 mm and most preferably approximately 0.8 mm. Radial orientation portions 42 are approximately 1.6 to 4.5 mm, but preferably approximately 2.0 to 4.0 mm and most preferably approximately 3.0 mm in length measuring from the center of broad connecting portion 40 to the center of outer end 58.

Figure 7:
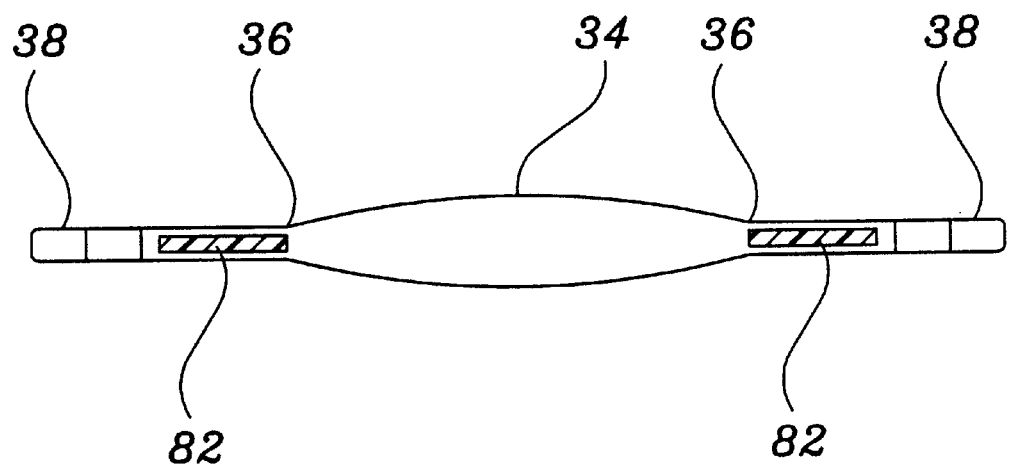
FIG. 7 is a side view of a looped haptic element of FIG. 2 taken along line 7—7 with a stiffening element therein.

The desired flexibility characteristic of looped haptic elements 38 of IOL 32 may likewise be achieved or enhanced by incorporating a stiffening element 82, in the shape of a ribbon, in looped haptic elements 38, as illustrated in FIG. 7. Stiffening elements 82 may be positioned in looped haptic elements 38 to function in a manner similar to that of an I-beam in construction to prevent axial displacement or tilting along optical axis OA—OA when compressive force is applied to looped haptic elements 38.

Stiffening elements 82 are formed of a less flexible material than that of IOL 32. Suitable materials for stiffening elements 82 include but are not limited to polyimides, polyolefins, high-density polyethylenes, polyesters, nylons, metals or any biocompatible material with suitable stiffening characteristics. Stiffening elements 82 may be used in conjunction with looped haptic elements 38 as described above or in cases where a thinner looped haptic design is desired while still achieving the desired flexibility characteristics.

Suitable materials for the production of the subject IOL 32 include but are not limited to foldable or compressible materials, such as silicone polymers, hydrocarbon and fluorocarbon polymers, hydrogels, soft acrylic polymers, polyesters, polyamides, polyurethane, silicone polymers with hydrophilic monomer units, fluorine-containing polysiloxane elastomers and combinations thereof. The preferred material for the production of IOL 32 of the present invention is either polyethylmethacrylate (PEMA) or a hydrogel made from 2-hydroxyethyl methacrylate (HEMA) and 6-hydroxyhexyl methacrylate (HOHEXMA), i.e., poly (HEMA-co-HOHEXMA). Poly(HEMA-co-HOHEXMA) is a preferred material for the manufacture of IOL 32 due to its equilibrium water content of approximately 18 percent by weight, and high refractive index of approximately 1.474, which is greater than that of the aqueous humor of the eye, i.e., 1.46. A high refractive index, i.e., above 1.33, is a desirable feature in the production of IOLs to impart high optical power with a minimum of optic thickness. By using a material with a high refractive index, visual acuity deficiencies may be corrected using a thinner IOL. Poly(HEMA-co-HOHEXMA) is also a desirable material in the production of IOLs 32 due to its mechanical strength, which is suitable to withstand considerable physical manipulation. Poly(HEMA-co-HOHEXMA) also has desirable memory properties suitable for IOL use. IOLs manufactured from a material possessing good memory properties such as those of poly(HEMA-co-HOHEXMA) unfold in a controlled manner in an eye, rather than explosively, to its predetermined shape. Explosive unfolding of IOLs is undesirable due to potential damage to delicate tissues within the eye. Poly(HEMA-co-HOHEXMA) also has dimensional stability in the eye.

Although the teachings of the present invention are preferably applied to soft or foldable IOLs formed of a foldable or compressible material, the same may also be applied to harder, less flexible lenses formed of a relatively rigid material such as polymethylmethacrylate (PMMA) having flexible haptics formed either of the same or a different material.

Optic portion 34 of IOL 32 can be a positive powered lens from 0 to approximately +40 diopters or a negative powered lens from 0 to approximately −30 diopters. Optic portion 34 may be biconvex, plano-convex, plano-concave, biconcave or concave-convex (meniscus), depending upon the power required to achieve the appropriate central and peripheral thickness for efficient handling.

Optic portion 34 of the subject IOL 32 may optionally be formed with a glare reduction zone 84 of approximately 0.25 to 0.75 mm but more preferably approximately 0.3 to 0.6 mm and most preferably 0.5 mm in width adjacent outer peripheral edge 36 for reducing glare when outer peripheral edge 36 of IOL 32 is struck by light entering eye 10 during high light or at other times when pupil 86 is dilated. Glare reduction zone 84 is typically fabricated of the same material as optic portion 34, but may be opaque, colored or patterned in a conventional manner to block or diffuse light in plane with optical axis OA—OA.

Subject IOL 32 is preferably manufactured by first producing discs from a material of choice as described in U.S. Pat. Nos. 5,217,491 and 5,326,506 each incorporated herein in its entirety by reference. IOL 32 may then be machined from the material discs in a conventional manner. Once machined, IOL 32 may be polished, cleaned, sterilized and packaged by a conventional method known to those skilled in the art.

Subject IOL 32 is used in eye 10 by creating an incision in cornea 12, inserting IOL 32 in posterior chamber 22 or anterior chamber 20 and closing the incision. Alternatively, IOL 32 may be used in eye 10 by creating an incision in cornea 12 and lens capsule 24, removing natural lens 16, inserting IOL 32 in lens capsule 24 and closing the incision.

IOL 32 of the present invention provides for a refractive lens suitable for use in lens capsule 24, posterior chamber 22 or anterior chamber 20. IOL 32 has looped haptic elements 38 with flexibility characteristics that minimize axial displacement or tilting along optical axis OA—OA of eye 10 thereby preventing decentration of IOL 32, distortion of vision and damage to delicate tissues within eye 10. IOL 32, having the flexibility characteristics described herein is also advantageous because one or a few lens sizes suitably fit eyes 10 of most sizes. By providing a "universal" lens such as that of the present invention, clinical risks to patients due to improperly sized lenses are minimized. Such clinical risks minimized include pupil ovalization, corneal endothelium damage and poor fixation. Likewise, manufacturers' need to produce IOLs of many sizes to fit eyes of many sizes is eliminated, thus reducing production and inventory costs associated therewith. Ophthalmologists also benefit from subject IOL 32 in that time is saved by eliminating the need to determine each patient's eye size and costs associated with maintaining large inventories of varying sized lenses.

While there is shown and described herein certain specific embodiments of the present invention, it will be manifest to those skilled in the art that various modifications may be made without departing from the spirit and scope of the underlying inventive concept and that the same is not limited to the particular forms herein shown and described except insofar as indicated by the scope of the appended claims.

We claim:

1. An intraocular lens to be implanted within an eye generally perpendicular to the eye's optical axis comprising:
    an outer peripheral edge defining an optic portion,
    two, or more balanced looped haptic elements permanently connected to the outer peripheral edge,
    two connectting portions on each looped haptic element to permanently connect looped haptic elements to said outer peripheral edge,
    a linking portion formed between each connecting portion, and
    a bow of less than 20 degrees toward said optic portion formed by said linking portion,
    whereby a compressive force sufficient to effect a 1.0 mm in diameter compression of said lens results in less than approximately 1.0 mm of axial displacement of said optic portion along the eye's optical axis.

2. An intraocular lens to be implanted within an eye generally perpendicular to the eye's optical axis comprising:
    an outer peripheral edge defining an optic portion,
    two, or more balanced looped haptic elements permanently connected to the outer peripheral edge,
    two connectting portions on each looped haptic element to permanently connect looped haptic elements to said outer peripheral edge,
    a linking portion formed between each connecting portion, and
    a bow of less than 20 degrees toward said optic portion formed by said linking portion,
    whereby a compressive force sufficient to effect a 1.0 mm in diameter compression of said lens results in less than approximately 0.5 mm of axial displacement of said optic portion along the eye's optical axis.

3. An intraocular lens to be implanted within an eye generally perpendicular to the eye's optical axis comprising:
    an outer peripheral edge defining an optic portion,
    two, or more balanced looped haptic elements permanently connected to the outer peripheral edge,
    two connectting portions on each looped haptic element to permanently connect looped haptic elements to said outer peripheral edge,
    a linking portion formed between each connecting portion, and
    a bow of less than 20 degrees toward said optic portion formed by said linking portion,
    whereby a compressive force sufficient to effect a 1.0 mm in diameter compression of said lens results in less than approximately 0.3 mm of axial displacement of said optic portion along the eye's optical axis.

4. The intraocular lens of claim 1, 2 or 3 wherein the looped haptic elements and the optic portion are both formed of a foldable or compressible material.

5. The intraocular lens of claim 1, 2 or 3 wherein said lens is formed from a material selected from the group consisting of silicone polymers, hydrocarbon and fluorocarbon polymers, hydrogels, soft acrylic polymers, polyester, polyamides, polyurethane, silicone polymers with hydrophilic monomer units, fluorine-containing polysiloxane elastomers and combinations thereof.

6. The intraocular lens of claim 1, 2 or 3 wherein said lens is formed from a hydrogel material.

7. The intraocular lens of claim 1, 2 or 3 wherein said lens is formed from a hydrogel material which is 18 percent by weight water.

8. The intraocular lens of claim 1, 2 or 3 wherein said lens is formed from poly(HEMA-co-HOHEXMA) or PEMA.

9. The intraocular lens of claim 1, 2 or 3 wherein said lens is formed from a material having a refractive index above 1.33.

10. The intraocular lens of claim 1, 2 or 3 wherein said lens is formed from an acrylic material.

11. The intraocular lens of claim 1, 2 or 3 wherein said lens is formed from a silicone material.

12. The intraocular lens of claim 1, 2 or 3 wherein said looped haptic elements are dimensioned to have a greater thickness in a plane generally perpendicular to the eye's optical axis than in a plane generally parallel to the eye's optical axis.

13. The intraocular lens of claim 1, 2 or 3 wherein a glare reduction zone is formed adjacent to the outer peripheral edge of the optic portion.

14. The intraocular lens of claim 1, 2 or 3 wherein said looped haptic elements include a stiffening element having a greater resistance to bending in a plane generally parallel to an eye's optical axis than in a plane generally perpendicular to the eye's optical axis.

15. The intraocular lens of claim 1, 2 or 3 wherein the looped haptic element includes a stiffening element formed from a material selected from the group consisting of polyimide, polyolefin, high-density polyester, nylon and metal.

16. A method of manufacturing the intraocular lens of claim 1, 2 or 3 comprising:

forming a disk of a suitable material, and
  machining said lens from said disk.

17. A method of using the intraocular lens of claim 1, 2 or 3 comprising:

creating an incision in a cornea of an eye, and
  inserting said intraocular lens in a posterior chamber or an anterior chamber of said eye.

18. A method of using the intraocular lens of claim 1,2 or 3 comprising:

creating an incision in a cornea and lens capsule of an eye,
  removing a natural lens of said eye, and
  inserting said intraocular lens in said lens capsule of said eye.

* * * * *